(12) United States Patent
Malin et al.

(10) Patent No.: US 6,236,047 B1
(45) Date of Patent: *May 22, 2001

(54) METHOD FOR MULTI-SPECTRAL ANALYSIS OF ORGANIC BLOOD ANALYTES IN NONINVASIVE INFRARED SPECTROSCOPY

(75) Inventors: Stephen F. Malin, Chanhassen, MN (US); Gamal Khalil, Chandler, AZ (US)

(73) Assignee: Instrumentation Metrics, Inc., Tempe, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/141,283

(22) Filed: Aug. 27, 1998

Related U.S. Application Data

(63) Continuation of application No. 08/597,480, filed on Feb. 2, 1996, now Pat. No. 6,040,578.

(51) Int. Cl.$^7$ ................................................. G01N 21/35
(52) U.S. Cl. ........................ 250/339.12; 250/339.11; 250/341.8
(58) Field of Search ........................ 250/339.12, 339.09, 250/339.11, 341.8; 600/316, 322, 347, 365

(56) References Cited

U.S. PATENT DOCUMENTS

| | | |
|---|---|---|
| 4,306,152 | 12/1981 | Ross et al. . |
| 4,427,889 | 1/1984 | Muller . |
| 4,491,730 | 1/1985 | Pedersen . |
| 4,655,225 | 4/1987 | Dahne et al. . |
| 4,805,623 | 2/1989 | Jobsis . |
| 4,882,492 | 11/1989 | Schlager . |
| 4,883,953 | 11/1989 | Koashi et al. . |
| 4,975,581 | 12/1990 | Robinson et al. . |
| 5,023,804 | 6/1991 | Hoult . |
| 5,054,487 | 10/1991 | Clarke . |

(List continued on next page.)

FOREIGN PATENT DOCUMENTS

| | | |
|---|---|---|
| 2 255 300 | 11/1972 | (DE) . |
| 43 39 067A1 | 11/1993 | (DE) . |
| 0 226 822 | 7/1987 | (EP) . |
| 0 426 358A1 | 8/1991 | (EP) . |
| 0 631 137A2 | 12/1994 | (EP) . |
| WO91/11136 | 8/1991 | (WO) . |
| WO92/17765 | 8/1992 | (WO) . |

OTHER PUBLICATIONS

Faber et al., "Generalized Rank Annihilation Method. III: Practical Implementation", *Jrn. of Chemometrics*, (1994), 8:273–285.

H.M. Heise et al., "Noninvasive Blood Glucose Sensors Based on Near–Infrared Spectroscopy", *Blackwell Scientific Pub., Inc.*, (1994), 18(6):439–447.

(List continued on next page.)

*Primary Examiner*—Seungsook Ham
*Assistant Examiner*—Richard Hanig
(74) *Attorney, Agent, or Firm*—Michael A. Glenn; Christopher Peil

(57) ABSTRACT

A method is described for determining the concentration of an organic blood analyte using multi-spectral analysis in the near infrared and mid-infrared ranges. Incident radiation containing a plurality of distinct, nonoverlapping regions of wavelengths in the range of approximately 1100 to 5000 nm is used to scan a sample. Diffusively reflected radiation emerging from the sample is detected, and a value indicative of the concentration of the analyte is obtained using an application of chemometrics techniques. Information obtained from each nonoverlapping region of wavelengths can be cross-correlated in order to remove background interferences.

16 Claims, 4 Drawing Sheets

U.S. PATENT DOCUMENTS

| | | |
|---|---|---|
| 5,070,874 | 12/1991 | Barnes et al. . |
| 5,086,229 | 2/1992 | Rosenthal et al. . |
| 5,121,337 | 6/1992 | Brown . |
| 5,146,091 | 9/1992 | Knudson . |
| 5,209,231 | 5/1993 | Cote et al. . |
| 5,222,495 | 6/1993 | Clarke et al. . |
| 5,222,496 | 6/1993 | Clarke et al. . |
| 5,242,602 | 9/1993 | Richardson et al. . |
| 5,252,829 | 10/1993 | Nygaard et al. . |
| 5,267,152 | 11/1993 | Yang et al. . |
| 5,349,189 | 9/1994 | Maggard . |
| 5,355,880 | 10/1994 | Thomas et al. . |
| 5,360,004 | 11/1994 | Purdy et al. . |
| 5,435,309 | 7/1995 | Thomas et al. . |
| 5,459,317 | 10/1995 | Small et al. . |
| 5,460,177 | 10/1995 | Purdy et al. . |
| 5,553,613 * | 9/1996 | Parker .................................. 600/316 |

OTHER PUBLICATIONS

Walter Lindberg et al., "Multivariate Resolution of Overlapped Peaks in Liquid Chromatography Using Diode Array Detection", *Anal. Chem.*, (1986), 58:299–303.

Lois A. Marquardt et al., "Near–Infrared Spectroscopic Measurement of Glucose in a Protein Matrix", *Anal. Chem.*, (1993), 65:3271–3278.

H. Zeller et al., "Blood Glucose Measurement by Infrared Spectroscopy", *Blackwell Scientific Pub Inc* (1989) 12(2):129–135.

* cited by examiner

METHOD FOR MULTI-SPECTRAL ANALYSIS OF ORGANIC BLOOD ANALYTES IN NONINVASIVE INFRARED SPECTROSCOPY this application is a continuation of Ser. No. 08/597,480 filing date of Feb. 2, 1996 U.S. Pat. No. 6,040,578.

TECHNICAL FIELD

The present invention relates to a method and apparatus for determining the concentration of a target analyte in a sample using multi-spectral analysis. The invention finds application in a wide range of chemical analyses, and particularly in noninvasive spectrophotometric analysis of blood analytes.

BACKGROUND OF THE INVENTION

The measurement of the concentration of various blood constituents finds application in a wide variety of procedures for the diagnosis and treatment of conditions and disease in human subjects. One important application is in the measurement of blood glucose. Specifically, the concentration of blood glucose should be monitored on a periodic basis in persons suffering from diabetes, and with respect to insulin-dependent or Type I diabetes, it is often necessary or desirable to monitor blood glucose several times a day. Further, the measurement of blood cholesterol concentrations provides important information in the treatment or prevention of persons suffering from coronary artery disease, and the measurement of other organic blood analytes, such as bilirubin and alcohol, is important in various diagnostic contexts.

The most accurate and widely practiced method of obtaining blood analyte concentrations involves the extraction of blood from a patient, which blood is then analyzed, either in a laboratory using highly accurate and sensitive assay techniques, or by the use less accurate self-testing methods. In particular, traditional blood glucose monitoring methods require the diabetic to draw a blood sample (e.g., by a finger-tip lance) for each test and to read the glucose level using a glucometer (a spectrophotometer that reads glucose concentrations) or a calorimetric calibration method. Such invasive blood extractions create a painful and tedious burden to the diabetic and expose the diabetic to the possibility of infection, particularly in light of the frequency of testing which is necessary. These considerations can lead to an abatement of the monitoring process by the diabetic.

Accordingly, there is a recognized need in the art for a simple and accurate method and device for noninvasively measuring blood analyte concentration, particularly in the context of blood glucose monitoring by diabetics. One approach to the problem entails the use of traditional methods of near infrared (near-IR) analysis, wherein the measurement of absorbance at one or more specific wavelengths is used to extract analyte-specific information from a given sample.

Near-IR absorbance spectra of liquid samples contain a large amount of information about the various organic constituents of the sample. Specifically, the vibrational, rotational and stretching energy associated with organic molecular structures (e.g., carbon-carbon, carbon-hydrogen, carbon-nitrogen and nitrogen-hydrogen chemical bonds) produces perturbations in the near-IR region which can be detected and related to the concentration of various organic constituents present in the sample. However, in complex sample matrices, near-IR spectra also contain an appreciable amount of interferences, due in part to similarities of structure amongst analytes, relative levels of analyte concentration, interfering relationships between analytes and the magnitude of electronic and chemical "noise" inherent in a particular system. Such interferences reduce the efficiency and precision of measurements obtained using near-IR spectrometry to determine the concentration of liquid sample analytes. However, a number of near-IR devices and methods have been described to provide noninvasive blood analyte determinations.

U.S. Pat. No. 5,360,004 to Purdy et al. describes a method and apparatus for the determination of blood analyte concentrations, wherein a body portion is irradiated with radiation containing two or more distinct bands of continuous-wavelength incident radiation. Purdy et al. emphasize filtration techniques to specifically block radiation at the two peaks in the NIR absorption spectrum for water, occurring at about 1440 and 1935 nm. Such selective blocking is carried out in order to avoid a heating effect that may be due to the absorption of radiation by water in the body part being irradiated.

By contrast, U.S. Pat. No. 5,267,152 to Yang et al. describes noninvasive devices and techniques for measuring blood glucose concentration using only the portion of the IR spectrum which contains the NIR water absorption peaks (e.g., the "water transmission window," which includes those wavelengths between 1300 and 1900 nm). Optically controlled light is directed to a tissue source and then collected by an integrating sphere. The collected light is analyzed and blood glucose concentration calculated using a stored reference calibration curve.

Devices have also been described for use in determination of analyte concentrations in complex samples.

For example, U.S. Pat. No. 5,242,602 to Richardson et al. describes methods for analyzing aqueous systems to detect multiple active or inactive water treating components. The methods involve determination of the absorbance or emission spectrum of the components over the range of 200 to 2500 nm, and application of chemometrics algorithms to extract segments of the spectral data obtained to quantify multiple performance indicators.

U.S. Pat. No. 5,252,829 to Nygaard et al. describes a method and apparatus for measuring the concentration of urea in a milk sample using an infrared attenuation measuring technique. Multivariate techniques are carried out to determine spectral contributions of known components using partial least squares algorithms, principal component regression, multiple linear regression or artificial neural network learning. Calibration is carried out by accounting for the component contributions that block the analyte signal of interest. Thus, Nygaard et al. describe a technique of measuring multiple analyte infrared attenuations and compensating for the influence of background analytes to obtain a more accurate measurement.

U.S. Pat. No. 4,306,152 to Ross et al. describes an optical fluid analyzer designed to minimize the effect of background absorption (i.e., the overall or base level optical absorption of the fluid sample) on the accuracy of measurement in a turbid sample or in a liquid sample which is otherwise difficult to analyze. The apparatus measures an optical signal at the characteristic optical absorption of a sample component of interest and another signal at a wavelength selected to approximate background absorption, and then subtracts to reduce the background component of the analyte-dependent signal.

The accuracy of information obtained using the above-described methods and devices is limited by the spectral interference caused by background, i.e., non-analyte, sample constituents that also have absorption spectra in the near-IR range. Appreciable levels of background noise represent an inherent system limitation, particularly when very little analyte is present. In light of this limitation, attempts have been made to improve signal-to-noise ratios, e.g., by avoiding water absorption peaks to enable the use of increased radiation intensity, by reducing the amount of spectral information to be analyzed, or by using subtraction or compensation techniques based on an approximation of background absorption. Although such techniques have provided some improvement, there remains a need to provide a method and apparatus capable of rendering a more precise determination of the concentration of analytes in a liquid matrix, particularly in the context of blood glucose monitoring.

SUMMARY OF THE INVENTION

Accordingly, it is a primary object of the invention to address the above-described needs in the art, by providing a method of determining the concentration of an analyte present in a sample having a varying background matrix and possibly having substantial component interferences as well. The method accounts for the similarity of structures among various components present in the sample, the relative magnitude of the analyte concentration and spectral interferences provided by various sample components and instrumentation variances.

The method generally involves: (1) identifying several distinct, nonoverlapping regions of wavelengths in the range of approximately 1100 to 3500 nm which have high correlation to the concentration of the analyte; (2) irradiating a sample with incident radiation containing those regions in order to obtain radiation that has been spectrally attenuated as a result of interaction with sample constituents; (3) detecting the spectrally attenuated radiation; (4) measuring the intensity of the spectrally attenuated radiation at a wavelength in nonoverlapping regions of wavelengths; and (5) correlating the measurements to obtain a value indicative of the concentration of the analyte.

In one aspect of the invention, a method is provided wherein spectral data from both the near infrared and the mid-infrared regions are analyzed to obtain analyte-specific information. Thus, the method involves the identification of several distinct, nonoverlapping regions of wavelengths in the range of approximately 1100 to 5000 nm which are substantially correlated with the concentration of the selected analyte or provide information about measurement and instrumentation parameters.

In another aspect of the invention, a method is provided which generally involves: (1) selecting several distinct, nonoverlapping regions of wavelengths from the infrared ranges spanning 1100–5000 nm which have high correlation to the concentration of the analyte; (2) irradiating a sample using infrared light containing the selected spectral ranges to obtain spectrally modified radiation; (3) optically filtering the spectrally modified radiation to isolate or emphasize a portion of the radiation from each nonoverlapping region; (4) collecting and measuring the intensity of the optically filtered radiation using a detector; and (5) obtaining a value indicative of the analyte concentration by applying a defined mathematical model to the optically filtered radiation.

It is also an object of the invention to provide a spectrophotometric apparatus for determining the concentration of an analyte present in a sample having a varying background matrix and substantial component interferences. The apparatus is configured to include an arrangement of detectors capable of collecting and measuring attenuated radiation reflected from a sample. The apparatus is used in a multispectral analysis to obtain spectral information containing analyte-specific signals as well as signals related to instrument background noise and interfering spectral information. Chemometrics techniques are used to configure filter elements capable of enhancing the correlation of analyte-specific information with the concentration of the analyte and to derive system algorithms capable of determining analyte concentration values. In one aspect of the invention, a diffraction grating system is used to obtain analyte-specific spectral information which is detected by a linear detector array capable of analyzing up to several hundred data points or wavelengths simultaneously.

DETAILED DESCRIPTION OF THE PREFERRED EMBODIMENTS

Figure 1A:
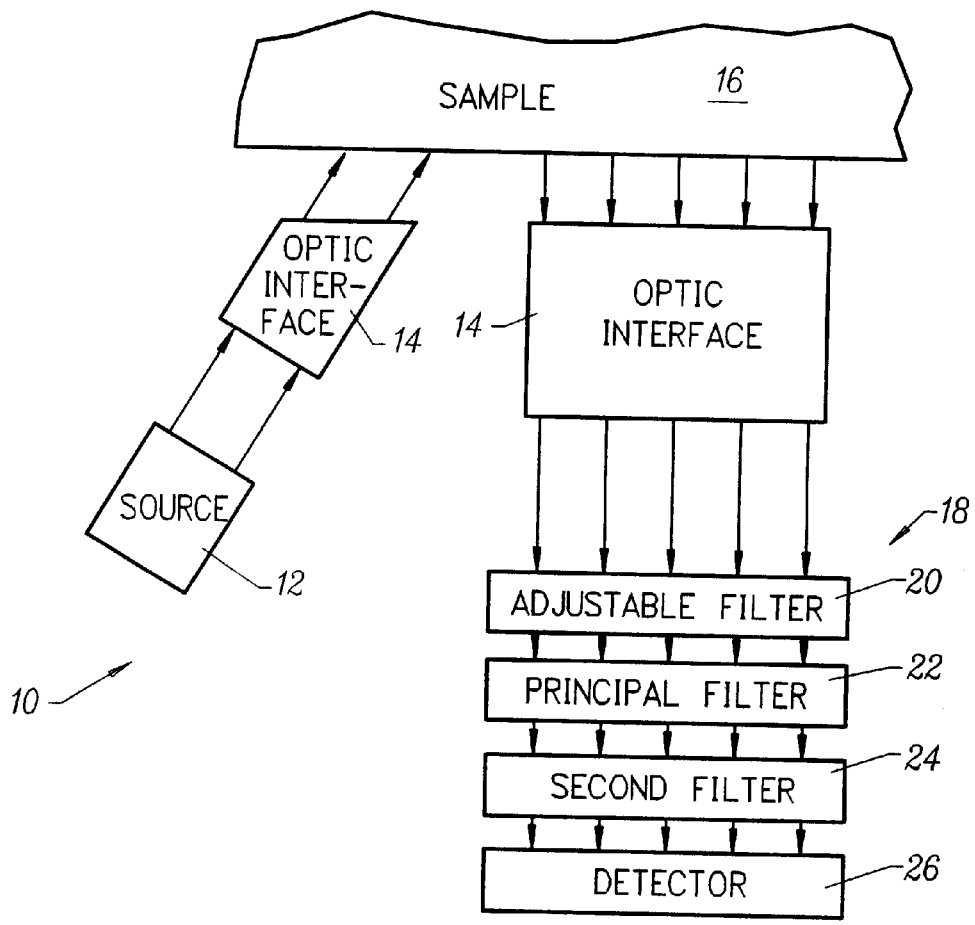
FIG. 1A is a diagrammatic representation of an apparatus constructed according to the invention having a linear array of detectors capable of analyzing wavelengths in both the near infrared and mid infrared regions.
Figure 1B:
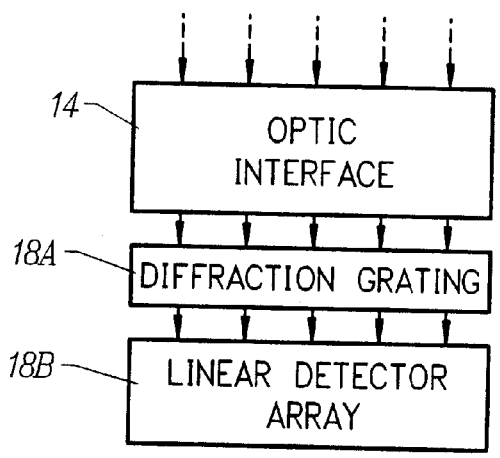
FIG. 1B is a diagrammatic representation of an apparatus constructed according to the invention having a diffraction grating and a linear detector array.

Before the invention is described in detail, it is to be understood that this invention is not limited to the particular component parts of the devices or methods described, as such may vary. It is also to be understood that the terminology used herein is for purposes of describing particular embodiments only, and is not intended to be limiting. It must be noted that, as used in the specification and the appended claims, the singular forms "a," "an" and "the" include plural referents unless the context clearly dictates otherwise. Thus, for example, reference to "an analyte" includes mixtures of analytes, reference to "an optical transfer cell" includes two or more optical transfer cells, "a means for reflectively transmitting radiation" includes two or more such means, "a wavelength" includes two or more wavelengths, "a chemometrics algorithm" includes two or more algorithms, and the like.

In this specification and in the claims which follow, reference will be made to a number of terms which shall be defined to have the following meanings:

"Chemometrics" relates to the application of mathematical, statistical and pattern recognition techniques in chemical analysis applications. See, e.g., Brown et al. (1990) *Anal. Chem.* 62:84–101. Chemometrics is practiced herein in the context of developing and using noninvasive diagnostic instrumentation that employs advanced signal processing and calibration techniques. Signal processing is used to improve the accessibility of physically significant information in analytical signals. Examples of signal processing techniques include Fourier transformation, first and second derivatives, and digital or adaptive filtering.

In the context of chemometrics, "calibration" refers to the process of relating data measurements to a chemical concentration for the purpose of quantification. Particularly, statistical calibrations using chemometric methods can be used to extract specific information from a complex set of data. Such methods of calibration include linear regression, multiple-linear regression, partial linear regression, and principal components analysis. In other applications, calibrations can be carried out using artificial neural networks, genetic algorithms and rotated principal components analysis.

Instrumentation that detects information for one or more constituents in a complex chemical matrix must rely upon analysis algorithms (such as those derived using chemometrics) in order to reveal information that is specific for one or more chemical constituent. Chemometrics techniques can be used to compare unknowns with calibrated standards and data bases to provide advanced forms of cluster analysis, and to extract features from an unknown sample that can be used as information in statistical and mathematical models. "Principal components analysis" (PCA) is one method of data reduction which can be performed in the application of chemometric techniques to spectroscopic measurement of chemical analytes in a complex matrix. PCA is used to reduce the dimensionality of a large number of interrelated variables while retaining the information that distinguishes one component from another. This reduction is effected using an eigenvector transformation of an original set of interrelated variables (e.g., an absorption spectrum) into a substantially smaller set of uncorrelated principal component (PC) variables that represents most of the information in the original set. The new set of variables is ordered such that the first few retain most of the variation present in all of the original variables. See, e.g., Jolliffe, L. T., *Principal Component Analysis*, Sprinter-Verlag, New York (1986). More particularly, each PC is a linear combination of all the original measurement variables. The first is a vector in the direction of the greatest variance of the observed variables. The succeeding PCs are chosen to represent the greatest variation of the measurement data and to be orthogonal to the previously calculated PC. Therefore, the PCs are arranged in descending order of importance.

The term "weighting constant" includes the wavelength coefficients of partial least squares regression and/or principal components regression, or any constant obtained from any statistical calibration that can be used to calculate values (such as analyte concentration) for unknown samples. A "wavelength weighting factor" is an embodiment of a weighting constant which is used in the construction of an optical filter means capable of emphasizing wavelength-specific information from spectral data. The wavelength-specific information can be used to determine desired values relating to the sample undergoing analysis (e.g., analyte concentration). A wavelength weighting factor can be embodied as a particular filter density (e.g., neutral or wavelength-specific), filter thickness, or the like, such parameters having been determined using the above-described statistical calibration techniques.

An optical filter means that embodies a wavelength weighting factor can be used to selectively emphasize wavelengths having high correlation with a selected analyte concentration. "High correlation" or "close correlation" refers to the quantitative association between the absorption spectrum at a particular wavelength and a particular analyte concentration, wherein the two variables have a correlation coefficient (r) of 0.9 or higher.

A "neutral density filter" refers to a standard optical filter means having a flat absorption spectrum. A neutral density filter can be used in concert with correlation filters in a filter system to provide a weighting factor to attenuate absorbance due to the analyte at selected wavelengths and further improve the accuracy of the correlation provided by the system. A neutral density filter can have an absorption spectrum sufficient to attenuate radiation equally at all wavelengths in the range of interest.

As used herein, an "aqueous medium" encompasses any composition containing water. Generally, an aqueous medium herein contains water as the major component, i.e., water is present in an amount of at least about 50 vol. %. Such aqueous media include, for example mammalian tissue.

The term "blood analyte" refers to a blood constituent that is absorbing in the near-IR range, the measurement of which is useful in patient monitoring or in the provision of health care.

As used herein, the term "near infrared" or "near-IR" encompasses radiation in a spectrum ranging from about 660 to about 3500 nm, more preferably from about 1050 to about 2850 nm, and most preferably from about 1100 to about 2500 nm.

The term "mid-infrared" or "mid-IR" encompasses radiation in a spectrum ranging from about 3501 nm to about 6000 nm.

The term "background absorption" relates to the overall or base level of optical absorption of an aqueous sample which is to be analyzed, from which the absorption of a selected constituent departs at one or more characteristic wavelengths to an extent indicative of the concentration of the selected constituent. When the level of background absorption is high in relation to the characteristic absorption of the selected constituent, such as in complex aqueous media where numerous interfering constituents are found, accurate measurement of the magnitude of a slight change in the absorption at the characteristic wavelength of a constituent of interest requires application of the chemometrics techniques described herein. This is particularly so in applications wherein the overall concentration of the constituent of interest is low relative to the aqueous medium, e.g., in the measurement of blood analytes.

General Methods

A spectrophotometric method is provided for determining the concentration of an analyte in a liquid sample using near- and mid-IR radiation. In contrast to prior techniques, the present method uses all of the spectral information contained in the near-IR region in order to obtain a set of measurements that can be used to determine an analyte concentration with a heightened degree of accuracy.

The method includes the steps of (1) selecting several distinct, nonoverlapping regions of wavelengths from the near-IR range spanning 1100–3000 nm, or from the near-IR range spanning 1100–3500 nm and the mid-IR range spanning 3501–5000 nm, wherein each region defines a spectral range, (2) irradiating a sample using infrared light containing the selected spectral ranges to obtain spectrally modified radiation which has been attenuated, (3) collecting and measuring the intensity of the spectrally attenuated radiation at one or more wavelengths contained within each of the selected spectral ranges, and (4) correlating those measurements to obtain a value indicative of the analyte concentration.

Spectral information obtained using this method can be subjected to a combination of mathematical transformations to arrive at a precise analyte concentration value. For example, standard statistical techniques, such as partial least squares (PLS) analysis, or principal components regression (PCR) analysis, can be used to correlate the absorbance of radiation at specific wavelengths to analyte structure and concentration. PLS techniques are described, for example, in, Geladi et al. (1986) *Analytica Chimica Acta* 185:1–17. For a description of PCR techniques, reference may be had to Jolliffe, L. T., *Principal Component Analysis*, Sprinter-Verlag, New York (1986).

Accordingly, in determining blood analyte concentration from a body tissue sample, one method involves the selection of three nonoverlapping regions of wavelengths from the near IR range spanning 1100 to 3500 nm; specifically, a first region spanning 1100 to 1350 nm, a second region spanning 1430 to 1450 nm or 1930 to 1959 nm, and a third region spanning 2000 to 2500 nm, wherein each region defines a "spectral range." The first region contains wavelengths in which proteins and other cellular components exhibit dominant spectral activity, the second region is dominated by the absorption spectrum of water, and the third region contains wavelengths in which organic analyte molecules exhibit significant spectral activity. These constituents also contribute to the absorption spectra in those regions where they are not the dominant species. Accordingly, the spectrally attenuated radiation obtained from each region contains a large amount of interrelated information that must be reduced using statistical methods to obtain analyte-specific information.

The invention also involves the use of signal processing to improve the accessibility of physically significant information in the analytical signals. The intensity values of signals obtained at particular wavelengths can thus be processed to reduce the effect of instrumentation noise. The processed signals are then subjected to multivariate analysis using known statistical techniques.

The PCA method of data reduction is one preferred method used in the practice of the invention to reduce the dimensionality of a large number of interrelated variables while retaining information that distinguishes one component from another. Data reduction is carried out using an eigenvector transformation of an original set of interrelated variables (e.g., the absorption spectrum) into a substantially smaller set of uncorrelated principal component (PC) variables that represents most of the information in the original set. The new set of variables is ordered such that the first few retain most of the variation present in the original set.

The principal component vectors can be transformed by orthogonal rotation against an average value for the absorbance to obtain both a known wavelength and the relative value of the absorbance at that wavelength which is attributable to the analyte. By performing this analysis on information obtained from each of the three spectral regions, cross-correlating the principal component vectors via a linear algorithm, and using subtractive methods to remove the effect of interfering analytes, values are obtained which can be used in a system algorithm to determine the concentration of the analyte.

Multivariate techniques are used to provide a model that relates the intensity of radiation at specific wavelengths in each spectral region to analyte concentrations in a particular sample matrix, e.g., body tissue. The model is constructed using two sets of exemplary measurements that are obtained simultaneously, the first set of measurements, the "prediction set," comprising spectral data, e.g., radiation intensity at selected wavelengths, and the second set of measurements, the "calibration set," comprising highly accurate analyte concentrations that have been determined using invasive sampling techniques. The procedure is carried out over a range of analyte concentrations to provide calibration and prediction data sets.

Measurements obtained in both the calibration set and the prediction set are subjected to multivariate analysis, such as by the use of commercially available multivariate model developing software programs, to provide an initial model. The initial model is applied to the prediction data to derive analyte concentration values that can be compared to the values obtained by the invasive techniques. By iteratively performing the above steps, a refined mathematical model is developed which can be used to establish a system algorithm for use in analyzing data obtained by the methods of the invention.

In the practice of the invention, non-analyte specific information from the various nonoverlapping spectral regions can be used, for example, to normalize each spectral scan, to subtract background and base line interferences, or to provide signal values used to detect an inaccurate measurement.

When determining a blood analyte concentration in a body tissue sample, measurements taken in the spectral range spanning approximately 1320–1340 nm provide a highly reflected, unattenuated, signal, as there are no major absorption bands present in the region. By collecting and measuring the intensity of radiation in that range, a value is obtained which can be used to estimate the actual intensity of the near-IR light used to irradiate the sample. The value can be used to normalize each individual scan and to correct for fluctuations in the intensity of the light source which could effect the accuracy of analyte concentration values obtained using the method of the invention.

Additionally, measurements taken in the spectral ranges spanning approximately 1430–1450 nm and approximately 1930–1950 nm provide substantially non-reflected, highly attenuated, signals, as a result of the two dominant absorption peaks occurring at about 1440 and 1935 nm in the near-IR absorption spectrum for water. By collecting and measuring the intensity of radiation in one or both of those ranges, a value is obtained which can be used to estimate the intensity of near-IR light that is not totally absorbed by the irradiated sample. The value can be used to subtract background or base-line information from the analyte-specific signals obtained in other regions and/or to provide an internal reference to detect inaccurate measurements. The value can be subtracted from each spectral measurement obtained using the present method in order to correct for the pedestal effect caused by specular reflection which varies with skin texture and age.

Measurements of substantially unattenuated signals obtained from a first region (e.g., the spectral range spanning approximately 1320–1340 nm) and measurements of highly attenuated signals obtained from a second region (e.g., the spectral ranges spanning approximately 1430–1450 nm and approximately 1930–1950 nm) can also be used to compare diffusely reflected radiation with specular radiation. If the signals in the two regions have relatively comparable values, it is likely that most of the radiation used to irradiate the tissue sample was reflected from the skin surface, and thus failed to penetrate the skin to interact with the blood analytes. This information can be used to identify ineffective measurements arising from a failure to obtain a proper instrumentation scan of the tissue sample.

In one aspect of the invention, a method of determining the concentration of an analyte in a sample is provided using non-invasive measurements obtained in several distinct, nonoverlapping regions of wavelengths in the infrared region and an optical processing system that is particularly suited for field or home applications. The method generally involves the steps of (1) selecting several distinct, nonoverlapping regions of wavelengths from the near-IR range spanning 1100–3000 nm, or from the near-IR range spanning 1100–3500 nm and the mid-IR range spanning 3501–5000 nm, wherein each region defines a spectral range, (2) irradiating a sample using infrared light containing the selected spectral ranges to obtain spectrally modified radiation, i.e., reflected radiation, (3) optically filtering the spectrally modified radiation to isolate or emphasize a portion of the radiation from each nonoverlapping region, (4) collecting and measuring the intensity of the optically filtered radiation using a detector, and (5) obtaining a value indicative of the analyte concentration by applying a defined mathematical model to the optically filtered radiation. The mathematical model can comprise a correlation algorithm obtained using the above-described chemometrics techniques.

The method of the invention can be carried out using a number of spectrophotometer configurations. Referring now to FIG. 1A, one particular apparatus for determining the concentration of an analyte in a liquid sample is generally indicated at 10. The apparatus includes a radiation source 12 which provides a plurality of distinct, nonoverlapping regions of wavelengths in the range of approximately of 1100 to 5000 nm. A number of suitable radiation sources are known in the art and can be used herein, e.g., incandescent light sources directed across interference filters, halogen light sources modulated by an associated chopper wheel, laser light sources, laser diode arrays, or high speed light-emitting diode (LED) arrays. In one particular apparatus, the radiation source 12 provides radiation at three distinct regions of wavelengths, specifically a first region of wavelengths in the approximate range of 1100 to 1350 nm, a second region in the approximate range of 1930 to 1950 nm and a third region in the approximate range of 2000 to 3500 nm.

The apparatus 10 also includes sample interface optic means 14 which launches incident radiation from the radiation source into contact with a sample medium 16 containing an analyte. After contacting the sample medium, spectrally modified radiation emerging from the sample as diffusively reflected light is collected and delivered to a multi-stage filter means, generally indicated at 18.

In various configurations, the sample interface optic means 14 can be designed to enable the close interface of the apparatus 10 with the medium 16, such as where the launch is carried out by placing the apparatus in direct contact with the sample medium, thereby bringing the radiation source into close proximity with the sample to be analyzed. After the launch, the reflected radiation is collected using optically active means, such as light converging means or beam deflection optics. Alternatively, the sample interface optic means 14 can comprise fiber optic waveguides coupled to the apparatus in order to enable remote apparatus placement and operation. Other configurations are provided wherein a single fiber optic bundle is employed to transmit the radiation to and from the medium. An optrode disposed at the end of the single bundle transmits the near-IR radiation to the sample medium 16 and receives spectrally modified radiation therefrom which is directed back through the bundle to the apparatus 10. Sapphire or high-grade quartz can be used as optical elements in the above fiber optic waveguides, as those materials have very good transmission characteristics in the near-IR spectral range.

Referring still to FIG. 1A, the reflected light emerging from the sample 16 passes to the multi-stage filter means 18. Specifically, the light passes to a first stage comprising an adjustable filter means 20 which is capable of having its absorption characteristics adjusted in response to a signal that is either externally generated, or that has been generated by the apparatus 10. The adjustable filter means generally comprises a screen filter, such as a neutral density filter, having absorption characteristics that are adjusted to variably attenuate the intensity of radiation as dictated by an external signal or system command. The degree of attenuation provided by the adjustable filter means 20 is based upon a predetermined factor selected to ensure that radiation emitted from the adjustable filter will be at a constant value regardless of the intensity of the pre-filtered radiation.

Attenuated radiation emerging from the adjustable filter means 20 is communicated to a principal analyte filter 22 which has optical characteristics capable of selectively passing one or more wavelengths from each of the distinct nonoverlaping regions of wavelengths launched by the radiation source 12. The wavelengths passed by the principal analyte filter are selected to have a correlation with the concentration of the analyte.

A second filter means 24 is arranged in the apparatus 10 relative to the principal analyte filter 22 such that selectively passed wavelengths emerging from the principal analyte filter interact with the second filter means. The second filter means has absorption characteristics selected such that the intensity of each passed wavelength is attenuated by the second filter means. The attenuations provided by the second filter means can be determined, for example, by an independent set of weighting factors derived using chemometrics techniques.

In one particular configuration, the weighting factors are determined using a partial least squares or principal component regression of an original spectrum obtained from a sample containing the analyte. The second filter means 24 can be constructed using a suitable substrate layer that is capable of transmitting radiation at least in the 1100 to 5000 nm range. The substrate layer is generally coated with one or more layers of metals and/or oxides that are conventional in the art to provide a plurality of second filter densities. Such coatings can be applied to the substrate using emulsion or chemical vapor deposition (CVD) techniques well known in the art. In an alternative apparatus, the second filter means is a photographic mask having spectral lines of optical density that are proportional to weighting functions determined using a rotated principal components or least squares analysis technique.

After attenuation by the second filter means, the independent wavelengths are communicated with a detection means 26, such as one or more Lead Sulfide (PbS) detectors, Gallium Arsenide detectors, or the like. In one particular apparatus configuration wherein it is desired to obtain measurements over the entire range of from about 1100 to 5000 nm, one or more Lead Selenide (PbSe) detectors can be used.

The detection means 26 detects and converts the attenuated wavelengths emitted from the second filter means into a signal which can then be applied toward an analyte specific algorithm to determine analyte concentration. Specifically, signals obtained from the second detection means can be readily converted into digital signals using an analog/digital converter. The digitized information is readily available for input into a microprocessor, or other electronic memory means, where it is used to provide an analyte concentration which can be visualized on a display device and/or recorded on an output recorder.

In an alternative configuration, the apparatus 10 can include a diffraction grating system 18A and a linear detector array 18B in place of the multi-stage filter means 18. Reflected light emerging from the sample 16 can be passed to a diffraction grating system configured to selectively pass discrete wavelengths therefrom, wherein the passed wavelengths are specifically correlated with the concentration of the analyte. The passed wavelengths are then communicated to a linear detector array, such as a PbS-based linear detector array or the like. In particular applications for obtaining measurements over the entire range of from about 1100 to 5000 nm, a PbSe-based linear detector array can be used. PbSe linear arrays can be obtained, for example, under the tradename MULTIPLEXIR™ (available from Graseby Infrared, Orlando, Fla.)

As described above, the linear detector array collects and measures the wavelengths passed by the diffraction grating system to provide signals which can be applied toward an analyte specific algorithm to determine analyte concentration.

The apparatus 10 can be used to obtain measurements of analyte concentration in a variety of complex media, such as in aqueous media having complex spectral backgrounds. In one application, the apparatus can be used in the determination of blood analyte concentrations, particularly organic blood analytes such as, but not limited to, glucose, urea (BUN), lipids, bilirubin and alcohol. The blood analyte can be present in an in vitro sample medium (e.g., a blood sample), or the apparatus can be used to measure blood analytes in tissue. However, the apparatus 10 is particularly adapted for use in field applications, e.g., in the measurement of blood alcohol, or in home health monitoring, e.g., in blood glucose determination.

Figure 2A:
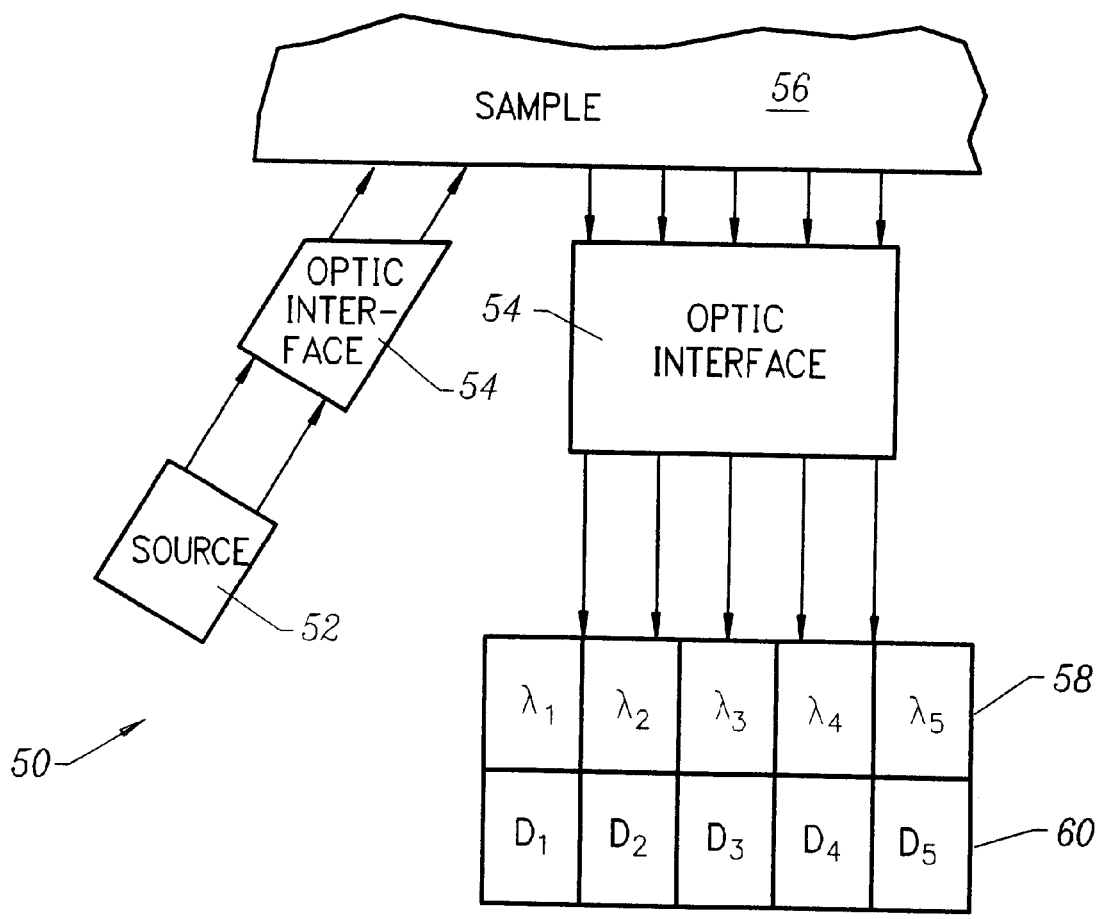
FIG. 2A is a diagrammatic representation of an alternative apparatus constructed according to the invention having a filter means.

Referring now to FIG. 2A, an alternative apparatus for determining the concentration of an analyte in a sample is indicated at 50. The apparatus includes a radiation source 52 which provides a plurality of distinct, nonoverlapping regions of wavelengths in the approximate range of 1100 to approximately 5000 nm. The apparatus 50 also includes sample interface optic means 54 which launches incident radiation from the radiation source into contact with a sample medium 56 containing an analyte. After contacting the sample medium, spectrally modified radiation emerging from the sample as diffusively reflected light is collected and delivered to a filter means 58 which is configured to pass light of specific wavelengths.

In operation, incident radiation is launched from the source 52 to the sample medium via sample interface optic means which, in one configuration, can be designed to enable the close interface of the apparatus with the particular sample medium being analyzed. After the launch, reflected radiation is collected using optically active means, such as a light converging means (i.e., a lens) or beam deflection optics. The sample interface optic means 54 can comprise fiber optic waveguides coupled to the apparatus 50 which enable remote apparatus placement and operation. As described above, one alternative system uses a single fiber optic bundle to transmit radiation to and from the medium.

The reflected radiation is directed to a filter means 58 which includes a plurality of discrete filter elements, indicated at $\lambda_1, \lambda_2, \lambda_3, \ldots \lambda_n$. The filter means 58 passes a population of selected wavelength ranges which provide analyte-specific information, information about the measurement background and information that can be used to correct for instrument changes or interference effects. The selected wavelengths emerging from the filter means are detected by an arrangement of detectors 60, having a plurality of discrete detector units generally indicated at $D_1, D_2, D_3, \ldots D_n$. The detectors are arranged such that each selected wavelength range emerging from the filter means is detected by a single, discrete detector. Suitable detector configurations are known in the art and can include, for example, an arrangement of PbS or PbSe detectors. Each detector converts the detected radiation into an electrical signal which can be used to obtain a value indicative of analyte concentration.

Signals obtained from the detectors can be readily converted into digital signals, e.g, digital signals indicative of the intensity of the detected wavelengths, using an analog/digital converter. The digitized information is then available for input into a microprocessor for further processing (e.g., applied to a system algorithm), or the information can be visualized via an electronic display means. Analog signals obtained from each discrete detector are communicated to an analog/digital (A/D) converter for conversion to digital form. The analog signals may be pre-amplified prior to conversion using techniques known in the art. Digital information from the A/D converter is then readily input into a microprocessor to calculate the analyte concentration using a system algorithm that is specific for the analyte. The microprocessor calculates analyte concentration by application of a chemometrics algorithm to the detected signals. Analyte-specific algorithms can be determined using iterative calibration and statistical modeling techniques, such as the above-described chemometrics methods.

In the practice of the invention, the filter means 58 can be constructed to include at least one discrete filter element having an absorption characteristic capable of providing enhanced correlation of the passed wavelength with the concentration of the analyte. Specifically, the filter means can include one or more filter elements which attenuate the intensity of a passed wavelength as determined, for example, by an independent set of weighting factors derived using chemometrics techniques. Such weighting factors can be derived using a partial least squares or principal component regression of an original spectrum obtained from a sample containing the analyte.

Figure 2B:
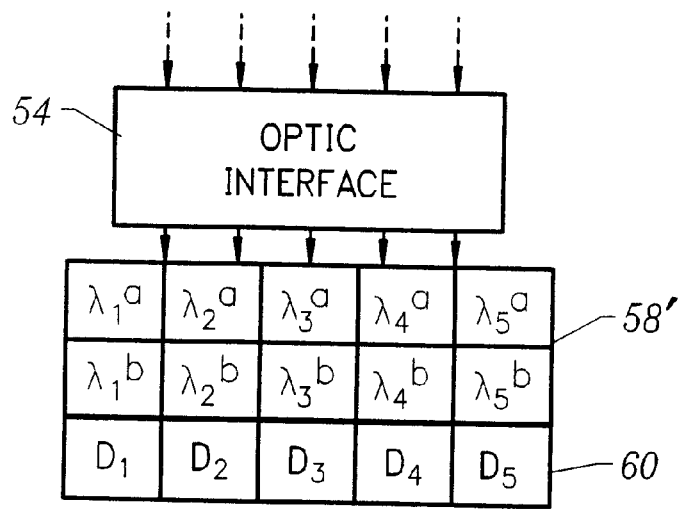
FIG. 2B is an alternate embodiment of the invention in which the filter means is a two-stage filter.

In another alternative configuration, the filter means 58 comprises a two-stage filter, 58', as illustrated in FIG. 2B the first stage includes a plurality of sections configured to selectively pass a population of selected wavelength ranges from the attenuated radiation reflected from the sample. The selectively passed wavelengths include analyte-specific information, information about the measurement background and information that can be used to correct for instrument changes or interference effects. The second stage of the filter is arranged directly adjacent to the first stage, and serves to attenuate the intensity of each of the passed wavelengths emerging from the first stage. The second stage of the two-stage filter means can be a neutral density filter having a flat absorption spectrum that is sufficient to equally attenuate the intensity of each of the passed wavelengths emerging from the first stage of the filter.

The apparatus 50 can be used to ascertain the concentration of one or more analytes of interest present in a variety of complex mediums, such as in an aqueous medium having a complex spectral background. Specifically, the apparatus can be used in the determination of blood analyte concentrations, particularly organic blood analytes such as, but not limited to, glucose, urea (BUN), lipids, bilirubin and alcohol. As described above, analysis of blood analyte concentrations can be conducted using in vitro samples, or an analysis can be carried out using a near-IR scan of tissue, such as reflective measurements obtained from a forearm tissue scan.

When the apparatus 50 is used to obtain blood analyte measurements from a tissue source, incident radiation launched from the source 52 via sample interface optic means 54 is caused to impinge upon the skin surface of tissue, such as upon a subject's forearm. The sample interface optic means directs the radiation at an angle toward the tissue such that it is absorbed by the tissue material near the surface and reflected as diffuse radiation. The incident radiation is spectrally modified as a result of infrared absorptions by the blood and tissue constituents. Portions of the incident near-IR radiation are absorbed, dispersed, diffused and reflected from the blood constituents present within the tissue source. This spectrally modified radiation contains information specific for each optically active blood constituent.

In determining blood glucose levels using the apparatus 50, vibrational motions of blood glucose molecules can be detected and measured using diffuse-reflective near-IR radiation. The vibrational motion includes both rotational and translational motion of the glucose molecules, including overtone vibrations and combined vibrations. Of these motions, the overtone vibrations are dominant and occur in the range of approximately 1670 to 1690 nm. The glucose combination vibration bands occur in the range of approximately 2120 to 2280 nm. Glucose does not have significant optical activity in the near-IR range of approximately 1320 to 1340 nm.

Accordingly, the apparatus 50 can include a filter means 58 having four distinct sections, where the first section is configured to pass reflected radiation from the region of wavelengths in the range of approximately 1300 to 1360 nm, the second section is configured to pass reflected radiation from the region of wavelengths, either in the range of approximately 1430 to 1450 nm, or approximately 1930 to 1950, the third section is configured to pass reflected radiation from the region of wavelengths in the range of approximately 1670 to 1690, and the fourth section is configured to pass reflected radiation from the region of wavelengths in the range of approximately 2120 to 2280 nm.

The intensity of wavelengths passed by the third and fourth sections of the filter means contains analyte-specific information. As described above, the third and fourth filter sections can be configured to include weighting factors which enhance the correlation of the passed radiation with the concentration of glucose present in the tissue sample. Information obtained from the first section of the filter can be used to estimate the background spectral contributions in each measurement, and can thus be used to correct or normalize the measurements obtained from the third and fourth filter sections. The signals obtained from the second filter section (the water absorption information) can be used as an internal check to identify ineffective measurements, e.g., those arising from a failure to obtain a proper instrumentation scan of the tissue sample, or the information can be used to correct for temperature changes in the measurements obtained from the third and fourth filter sections.

It is to be understood that while the invention has been described in conjunction with preferred specific embodiments thereof, the foregoing description, as well as the examples which follow, are intended to illustrate and not limit the scope of the invention. Other aspects, advantages and modifications within the scope of the invention will be apparent to those skilled in the art to which the invention pertains.

EXAMPLE

A noninvasive glucose measurement was obtained using the method of the invention. Particularly, reflective optical measurements in the near-IR region of approximately 1100 nm to 3500 nm were carried out. Spectral scans were collected from volunteer forearm subjects, using an instrument having a Tungsten-Mercury (W-Hg) radiation source, a Lead Sulfide (PbS) detector and a scan speed of nm / 0.4 second.

Figure 3:
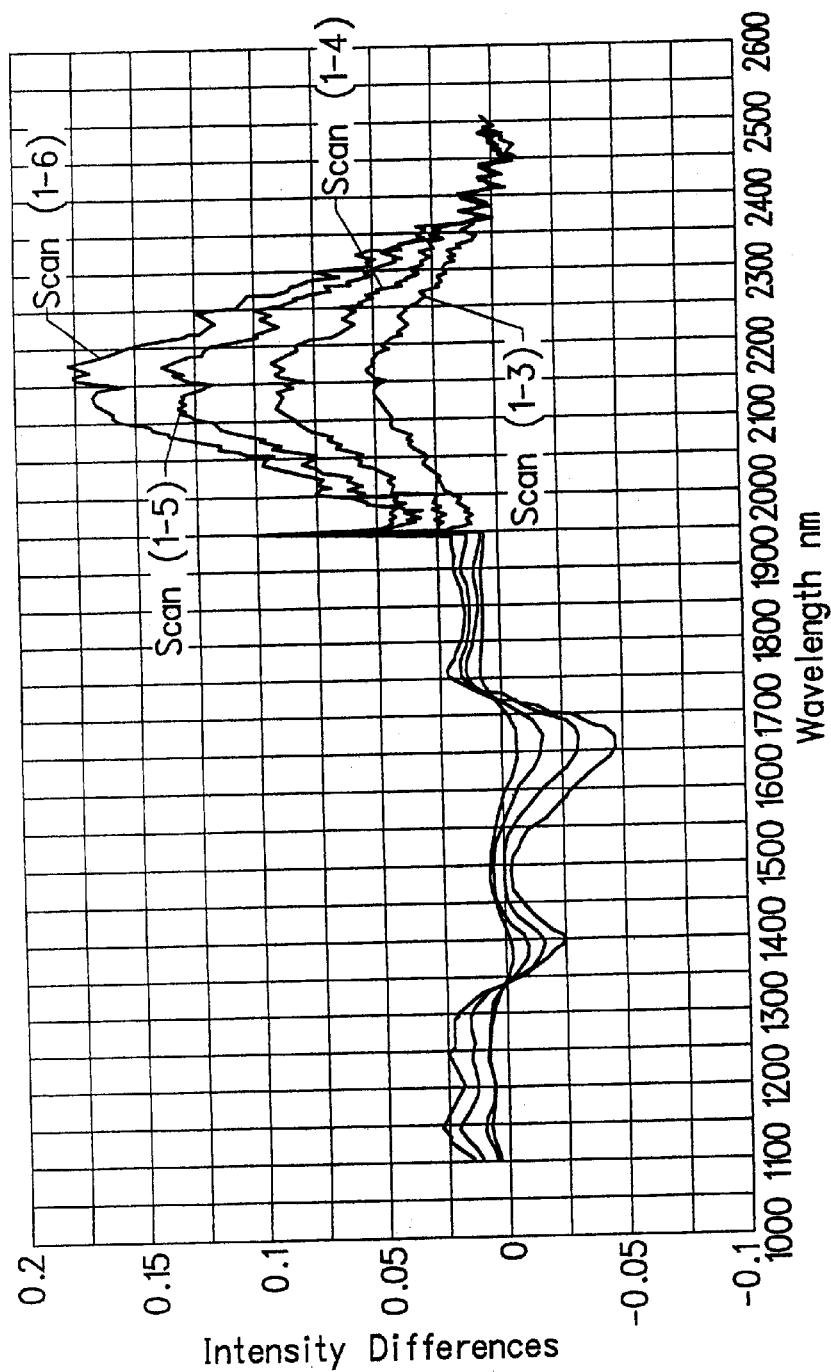
FIG. 3 is a graph illustrating time-dependent scans taken during an in vivo glucose tolerance study.

A number of specific spectral ranges were identified as containing information which can be used to determine glucose concentration from a forearm tissue scan. The specified regions were determined from an in vivo glucose tolerance study conducted in tandem with invasively-obtained in vitro blood glucose concentration determinations. In particular, time-dependent scans taken during the in vivo tolerance study are depicted in FIG. 3. As can be seen, significant changes in the reflective intensity differences over the range of about 2120 to 2180 nm were recorded during the time course of the study. These changes increased in direct relation to increases in blood glucose level during the tolerance test, signifying that the range of 2120 to 2180 nm contains glucose-specific spectral information.

Once the specific spectral ranges were identified, noninvasive glucose measurements were obtained using information from the four distinct spectral ranges. The first spectral range included radiation occurring at about 1320 to 1340 nm. This range provides a very highly reflected signal, and there is no major glucose absorption band in this range. Information obtained from the first spectral range can be used to normalize each individual scan in order to correct for fluctuations in the radiation source, and changes due to mechanical perturbations.

The second spectral range included radiation occurring at either about 1440 to 1460 nm, or about 1940 to 1960 nm. These ranges provide a substantially non-reflected signal due to the highly absorptive water bands which attenuate diffusively reflected radiation. Information obtained from these ranges can be used for background and base line subtraction from other measurements. These measurements allow for a pedestal adjustment to account for fluctuations induced by specular reflection signal values, and can be used to detect improper measurements.

The third range included radiation occurring at about 1670 to 1690 nm. This range provides analyte-specific information due to the presence of glucose vibrational overtone bands.

The fourth range included radiation occurring at about 2120 to 2280 nm. This range provides analyte-specific information due to glucose combination vibrational bands.

Signals obtained from the first range were used to normalize signals of other regions. This process, when repeated with each spectral scan, eliminates the problem associated with light source changes and serves to provide an internal reference. Measurement variations induced by differences in optical interface, e.g., patient placements, were accordingly substantially reduced.

Background information was eliminated by subtracting the signals obtained in the second range, from the signals obtained in the third and fourth analyte-specific ranges. In this manner, the pedestal effect created by specular reflection, which varies with skin texture and age, was corrected for.

Figure 4:
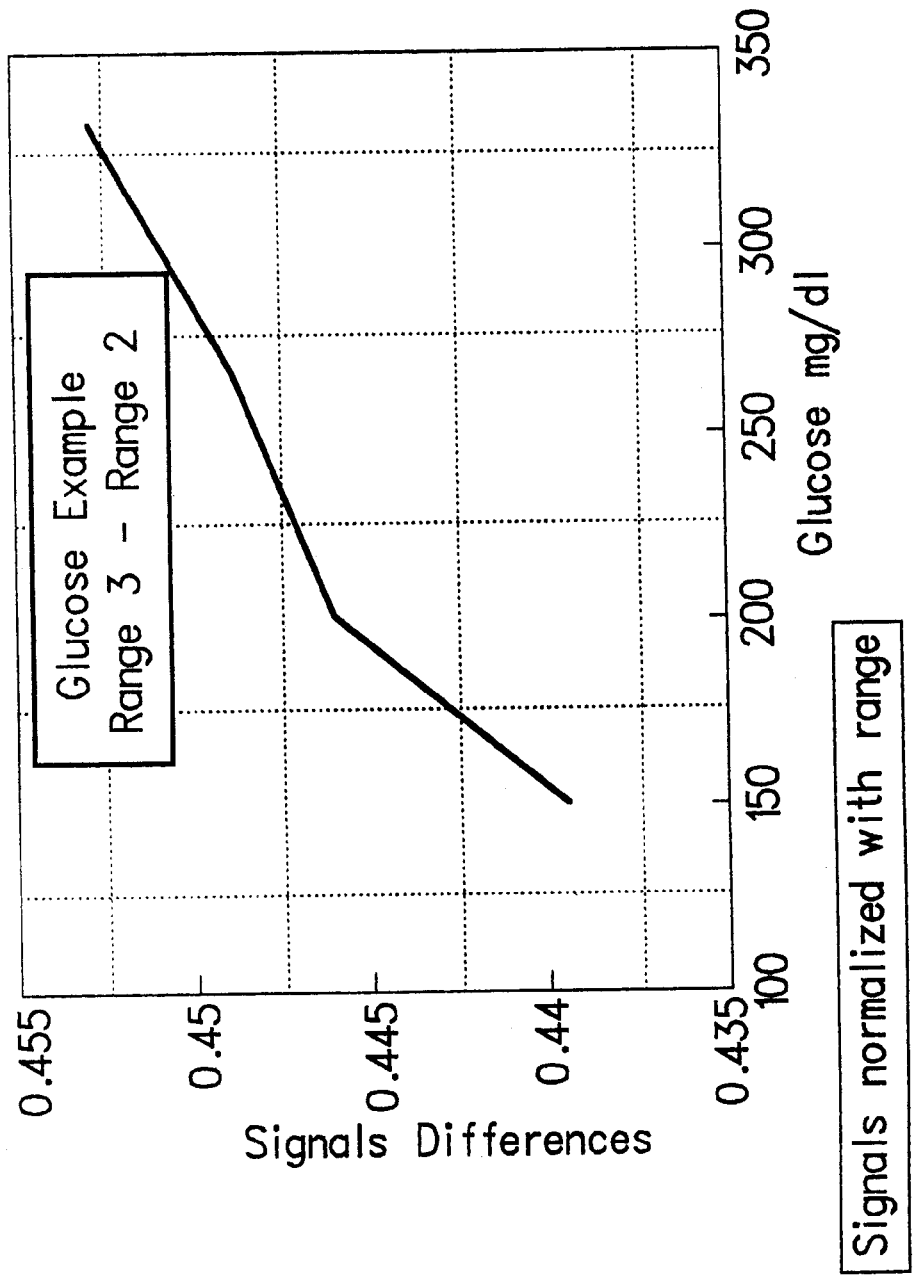
FIG. 4 depicts in graph form the results obtained from a noninvasive determination of blood glucose concentration conducted using the method of the invention.

The normalized and base line corrected signals from the third and fourth ranges were applied in an analytical chemometric analysis. FIG. 4 depicts the normalized differences between signals in the second and third ranges.

As can be seen by the results depicted in FIG. 4, increase in blood glucose level results in an increase in the signal differences between the two ranges.

What is claimed is:

1. A method of determining the concentration of an organic blood analyte in a body tissue sample, comprising:
   (a) selecting a plurality of distinct, nonoverlapping spectral regions within an infrared spectrum, wherein each of the spectral regions encompass a range of wavelengths between approximately 1100 and 5000 nanometers, and wherein at least a portion of each spectral region has high correlation to the concentration of the analyte;
   (b) irradiating the sample with light having a wavelength in each spectral region to obtain radiation reflected from and modified by contact with the sample in each spectral region;
   (c) optically filtering the reflected modified radiation to isolate or emphasize a portion of the radiation from each spectral region;
   (d) collecting and measuring the intensity of the optically filtered radiation using a detector means; and
   (e) obtaining a value indicative of the analyte concentration by applying a mathematical model to the optically filtered radiation.

2. The method of claim 1, wherein step (c) comprises passing the modified radiation through optical filter means having absorption characteristics capable of selectively passing discrete wavelengths from each spectral region, wherein said discrete wavelengths are specifically correlated with the concentration of the analyte.

3. The method of claim 2, wherein the absorption characteristics of the optical filter means are derived using chemometrics techniques.

4. The method of claim 1, wherein the detector means comprises a plurality of detectors.

5. The method of claim 4, wherein the plurality of detectors comprise lead selenide (PbSe) detectors.

6. The method of claim 1, wherein the organic blood analyte is selected from the group consisting of glucose, urea (BUN), lipids, bilirubin and ethyl alcohol.

7. The method of claim 6, wherein the blood analyte is glucose.

8. A method of determining the concentration of an organic blood analyte in a body tissue sample, comprising:
   (a) selecting a plurality of distinct, nonoverlapping spectral regions within an infrared spectrum, wherein each of the spectral regions encompass a range of wavelengths between approximately 1100 and 5000 nanometers, and wherein at least a portion of each spectral region has high correlation to the concentration of the analyte;
   (b) irradiating the sample with incident light having a wavelength in each spectral region to obtain radiation reflected from and attenuated by contact with the sample and radiation unattenuated by contact with the sample, wherein the attenuated radiation is contained within each spectral region;
   (c) collecting the reflected attenuated radiation;
   (d) measuring the intensity of the collected reflected attenuated radiation at a predetermined wavelength in each of the spectral regions; and
   (e) correlating the intensity measurements obtained in step (d) to determine a value indicative of the concentration of the analyte.

9. The method of claim 8, wherein the infrared spectrum contains a first spectral region of wavelengths in the range of approximately 1100 to 1350 nm, a second spectral region of wavelengths in the range of approximately 1550 to 1850 nm, and a third spectral region of wavelengths in the range of approximately 2000 to 3500 nm.

10. The method of claim 9, further comprising the steps of collecting and measuring the intensity of the unattenuated radiation, wherein said unattenuated radiation is from the first spectral region and contains wavelengths in the range of approximately 1320 to 1340 nm.

11. The method of claim 10, wherein the measure of the intensity of the unattenuated radiation is used to estimate the intensity of the incident light used in step (b).

12. The method of claim 10, wherein said reflected attenuated radiation includes highly attenuated radiation and wherein the highly attenuated radiation encompasses a band of wavelengths corresponding to a peak in the infrared absorption of water.

13. The method of claim 12, further comprising the steps of collecting and measuring the intensity of the highly attenuated radiation.

14. The method of claim 13, wherein the measure of the intensity of the highly attenuated radiation is used to estimate the intensity of the light not absorbed by the irradiated sample.

15. The method of claim 14, wherein the band of wavelengths corresponding to a peak in the infrared absorption spectrum of water is in the range of approximately 1430 to 1450 nm.

16. The method of claim 14, wherein the band of wavelengths corresponding to a peak in the infrared absorption spectrum of water is in the range of approximately 1930 to 1950 nm.

* * * * *